United States Patent [19]

Bauman

[11] Patent Number: 4,914,243
[45] Date of Patent: Apr. 3, 1990

[54] PRODUCTION OF 2-ALKOXY OR ARYL(LOWER)ALKOXY-6-METHOXY-1-NAPHTHALENECARBOXALDEHYDE

[75] Inventor: John G. Bauman, Windsor, N.J.

[73] Assignee: American Home Products Corporation, New York, N.Y.

[21] Appl. No.: 344,187

[22] Filed: Apr. 27, 1989

Related U.S. Application Data

[62] Division of Ser. No. 137,390, Dec. 23, 1987, Pat. No. 4,866,197.

[51] Int. Cl.$^4$ .......................................... C07C 41/548
[52] U.S. Cl. ..................................................... 568/433
[58] Field of Search ......................................... 568/433

[56] References Cited

U.S. PATENT DOCUMENTS 4,439,617 3/1984 Sestanj et al. .................... 560/39
4,568,693 2/1986 Sestanj et al. ...................... 514/524

FOREIGN PATENT DOCUMENTS 0277894 8/1988 European Pat. Off. ............ 568/433
2211436 9/1972 Fed. Rep. of Germany ...... 568/433
56-150034 11/1981 Japan .................................. 568/433

Primary Examiner—Bruce Gray
Attorney, Agent, or Firm—Walter Patton

[57] ABSTRACT

Process for the production of 2-alkoxy or aryl(lower)alkoxy-6-methoxy-1-naphthalenecarboxaldehyde chemical intermediates by demethylating 2,6-dimethoxy-1-naphthalenecarboxaldehyde with a nucleophilic sulfide reagent at the 2-position and reacting the resulting phenolate salt with an alkylating reagent. Said aldehydes are themselves intermediates for the manufacture of compounds which inhibit aldose reductase and are useful for the treatment of diabetic complications.

2 Claims, No Drawings

PRODUCTION OF 2-ALKOXY OR ARYL(LOWER)ALKOXY-6-METHOXY-1-NAPH-THALENECARBOXALDEHYDE

This is a divisional of co-pending application Ser. No. 137,390, filed on Dec. 23, 1987, now U.S. Pat. No. 4,866,197.

BACKGROUND OF THE INVENTION a. Field of Invention

This invention relates to novel processes for the production of N-(2-alkoxy-1-naphthoyl)glycine esters. The N-(2-alkoxy-1-naphthoyl)glycine esters produced by the present process are themselves useful intermediates for the manufacture of N-naphthoylglycine derivatives having aldose reductase inhibiting activity and which are useful for treating diabetic complications. Said aldose reductase inhibitors are described in copending patent application Ser. No. 397623, incorporated herein by reference.

More specifically this invention relates to the process for the production of N-[[2-alkoxy-6-methoxy-5-(trifluoromethyl)-1-naphthalenyl]carbonyl]-N-methylglycine esters of formula (I)

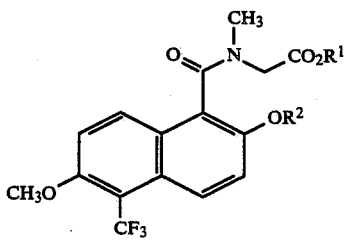

(I)

wherein $R^1$ and $R^2$ are lower alkyl or aryl(lower)alkyl, wherein lower alkyl contains 1 to 6 carbon atoms.

b. Prior Art

The closest prior art to the present invention is Sestanj et al, U.S. Pat. No. 4,439,617, Mar. 27, 1984; and Sestanj et al, U.S. Pat. No. 4,568,693, Feb. 4, 1986. Sestanj et al disclosed processes for preparing N-naphthoylglycine esters which are intermediates in the preparation of compounds which inhibit aldose reductase, but which lack a 2-alkoxy substituent on the naphthalene ring.

SUMMARY OF THE INVENTION

The process of the present invention is directed to the production of compounds of formula (I)

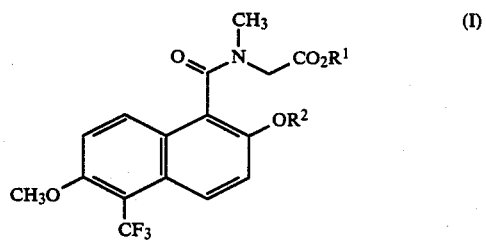

(I)

wherein $R^1$ and $R^2$ are lower alkyl or aryl(lower)alkyl wherein lower alkyl contains 1 to 6 carbon atoms. Compounds of formula (I) are intermediates in the synthesis of compounds which have aldose reductase inhibiting activity.

The processes of the present invention are represented by the following flow sheet:

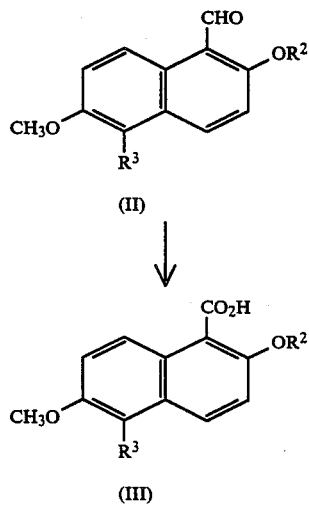

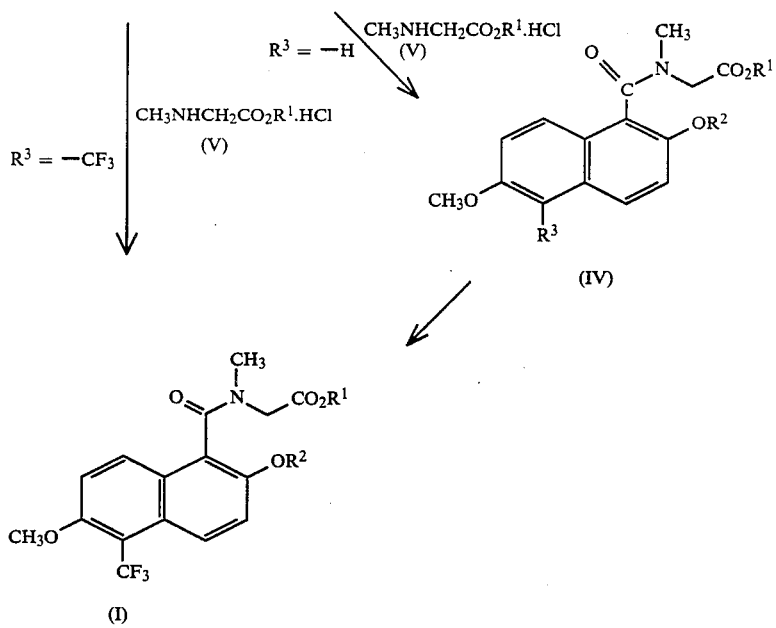

wherein $R^1$ and $R^2$ are lower alkyl or aryl(lower)alkyl wherein lower alkyl contains 1 to 6 carbon atoms, and $R^3$ is hydrogen, halogen or trifluoromethyl. Referring to the flow sheet, the process for preparing compounds of formula (I) comprises a. Reacting an aldehyde of formula (II) wherein $R^2$ and $R^3$ are as defined herein above with an oxidizing agent such as potassium permanganate or sodium chlorite in water and a water miscible and unreactive organic solvent or mixture of solvents such as acetone, p-dioxane, tetrahydrofuran or 2-methyl-2-propanol at a temperature between 0° C. and 100° C. to give an acid of formula (III).

More specifically, the preferred process involves reacting an aldehyde of formula (II), where $R^2$ and $R^3$ are as defined above with sodium chlorite in the presence of a "chlorine scavenger" such as resorcinol as described by B. Lindgren et al, Acta Chemica Scand., 27, 888 (1973) and an acid catalyst such as acetic acid in a mixture of water, p-dioxane and 2-methyl-2-propanol at a temperature between 20° C. and 100° C. which is sufficient to create a homogeneous reaction mixture.

The preferred process has the following advantages:
1. the reagents are inexpensive
2. the reaction mixture is homogeneous
3. the reaction is rapid, and dimerization and over oxidation are minimized
4. the "chlorine scavenger" serves to prevent chlorination of the electron rich aromatic nucleus when $R^3$ is hydrogen
5. the acid of formula (II) can be isolated in high yield and high purity.

b. Reacting the naphthoic acid (III) wherein $R^2$ and $R^3$ are as defined above with an N-methylglycine ester of formula (V) wherein $R^1$ is lower alkyl or aryl(lower-)alkyl wherein lower alkyl contains 1 to 6 carbon atoms, is done preferably by the "carboxyl activation" coupling procedure as described by Sestanj et al, U.S. Pat. No. 4,439,617. This process gives an N-naphthoylglycine of formula (IV) when $R^3$ is hydrogen or of formula (I) when $R^3$ is trifluoromethyl. The preferred activated form of the carboxyl group is the acid chloride which can be generated in situ, for example, by reacting the acid of formula (III) and oxalyl chloride, in a suitable solvent such as $CH_2Cl_2$ and preferably in the presence of a catalyst such as N,N-dimethylformamide.

More specifically, naphthalenecarboxaldehydes of formula (II), wherein $R^2$ is lower alkyl containing 2 to 6 carbon atoms or aryl(lower)alkyl wherein lower alkyl contains 1 to 6 carbon atoms and $R^3$ is hydrogen can be prepared from 2,6-dimethoxy-1-naphthalenecarboxaldehyde [formula (II) wherein $R^2$ is methyl and $R^3$ is hydrogen] which has been described by N. Buu-Hoï et al, J. Chem. Soc., 2776 (1955). Reaction of 2,6-dimethoxy-1-naphthalenecarboxaldehyde with a nucleophilic sulfide reagent such as sodium thiopropoxide in a solvent which is preferably N,N-dimethylformamide selectively cleaves the methyl-oxygen bond of the ether at the 2-position. The resulting phenolate salt may then be reacted directly with an alkylating agent of formula $R^2X$ wherein $R^2$ is the desired lower alkyl or aryl(lower)alkyl group and X is a "leaving group" such as bromine, iodine, $OSO_3R^2$, or a sulfonate.

More specifically, naphthalenecarboxaldehydes of formula (II) wherein $R^2$ is lower alkyl containing 1 to 6 carbon atoms or aryl(lower)alkyl wherein lower alkyl contains 1 to 6 carbon atoms and $R^3$ is hydrogen may be reacted with bromine in a suitable solvent such as acetic acid or $CH_2Cl_2$ to give the corresponding aldehyde wherein $R^3$ is bromine. Alternatively, naphthalenecarboxaldehydes of formula (II) wherein $R^3$ is iodine and $R^2$ is as defined above may be prepared by heating the corresponding aldehyde of formula (II) wherein $R^3$ is hydrogen, with iodine and an oxidizing agent such as iodic acid in a mixture of water and acetic acid with a catalytic amount of sulfuric acid.

Naphthalenecarboxaldehydes of formula (II) wherein $R^2$ is as defined above and $R^3$ is trifluoromethyl may be prepared by reacting an aldehyde of formula (II) wherein $R^2$ is as defined above and $R^3$ is either bromine or iodine with a trifluoromethyl transfer reagent and an apropriate copper catalyst. The preferred process involves heating a stirred suspension of a suitable copper (I) salt such as copper (I) iodide, sodium trifluoroacetate or a similar trifluoroacetate salt, and the aldehyde of formula (II) wherein $R^2$ is as defined above and $R^3$ is bromine or iodine in a polar aprotic solvent such as 1-methyl-2-pyrrolidinone under an inert atmosphere at between 170° C. and 200° C. until the substrate is consumed. Examples of other reagents which may accomplish this conversion include iodotrifluoromethane and copper metal as described by Sestanj et al in U.S. Pat. No. 4,439,617, bis-trifluoromethyl mercury as described by N. Kondratenko et al, Synthesis, 932 (1980) or bis-trifluoromethyl cadmium or bis-trifluoromethyl zinc as described by D. Burton et al, J. Am. Chem. Soc., 107, 5014 (1985).

In a preferred alternate process, the amido ester of formula (IV) wherein $R^1$ and $R^2$ are as defined above and $R^3$ is hydrogen may be halogenated according to the processes described hereinabove for the halogenation of aldehydes of formula (II), to give the corresponding compounds of formula (IV) wherein $R^3$ is either bromine or iodine. These halogenated compounds of formula (IV) may then be reacted with a trifluoromethyl transfer reagent as in the process described hereinabove for trifluoromethylation of the 5-halo aldehydes of formula (II) to give the corresponding 5-trifluoromethyl amido ester of formula (I).

The following examples further illustrate this invention.

EXAMPLE 1

Preparation of 2,6-Dimethoxy-1-naphthalenecarboxylic Acid

A solution of sodium chlorite (15.7 g, 80%, 0.139 mol) in 45 mL of water was added rapidly to a warm solution of 2,6-dimethoxy-1-naphthalenecarboxaldehyde [25.76 g, 0.119 mol, described by N. P. Buu-Hoï et al, J. Chem. Soc., 2776 (1955)], resorcinol (17.8 g, 0.162 mol) and acetic acid (0.25 g) in tert-butanol (115 mL) and p-dioxane (95 mL). The reaction temperature was maintained at about 85° C. for 10 minutes then allowed to cool and the mixture was concentrated under vacuum. The residue was partitioned between 1M KOH and dichloromethane. The phases were separated and the aqueous solution was acidified with 6N HCl and washed three times with dichloromethane. The acidic dichloromethane extracts were combined and washed with water and then with saturated sodium chloride and then dried over $Na_2SO_4$. After filtration and concentration, the residue was recrystallized from ethanol-water to give 23.1 g (84% yield) of 2,6-dimethoxy-1-naphthalenecarboxylic acid as an off-white solid, m.p. 153°–155° C.

NMR (200 MHz, $CDCl_3$): δ3.91 (s, 3H), 4.09 (s, 3H), 7.10 (d, J=2 Hz, 1H), 7.2–7.4 (m, 2H), 7.89 (d, 1H, J=9 Hz), 8.61 (d, 1H, J=9 Hz);

IR (KBr): 2950, 1690 cm$^{-1}$;

Anal. Calcd.: C, 67.18; H, 5.21%. Found: C, 67.37; H, 5.29%.

EXAMPLE 2

Preparation of N-[(2,6-Dimethoxy-1-naphthalenyl)carbonyl]-N-methylglycine Methyl Ester A solution of oxalyl chloride (0.95 mL, 11 mmol) in $CH_2Cl_2$ (10 mL) was added to a suspension of 2,6-dimethoxy-1-naphthalenecarboxylic acid (2.32 g, 10 mmol, described in Example 1) and N,N-dimethylformamide (2 drops, catalyst) in $CH_2Cl_2$ (50 mL) under nitrogen. After 1.5 hours, triethylamine (5 mL, 36 mmol) and N-methylglycine methyl ester hydrochloride (2.1 g, 15 mmol) were added. The resulting mixture was stirred at room temperature overnight and then poured into water (200 mL) and $CH_2Cl_2$ (200 mL). The aqueous phase was washed with $CH_2Cl_2$ (100 mL) and the combined $CH_2Cl_2$ phases were washed successively with 1M $H_3PO_4$ (2×100 mL), water (100 mL), saturated $NaHCO_3$ (50 mL), brine (100 mL) and dried over $Na_2SO_4$. Filtration and concentration left a pale brown foam which was filtered through a short column of silica gel with 1:1 ethyl acetate:hexane to obtain 2.53 g of the title compound as a pale yellow oil.

NMR (200 MHz, $CDCl_3$): δ2.87, 3.30 (2s, 3:1 ratio, 3H), 3.57–4.0 (m, 10H), 4.99 (d, 1H, J=17 Hz), 7.05–7.3 (m, 3H), 7.6–7.9 (m, 2H);

IR (neat): 2960, 1745, 1645 cm$^{-1}$;

High resolution mass spectrometry: $C_{17}H_{19}NO_5$ Requires: 317.1263. Found: 317.1259.

EXAMPLE 3

Preparation of N-[(5-Bromo-2,6-dimethoxy-1-naphthalenyl)carbonyl]-N-methylglycine Methyl Ester A solution of bromine (1.75 mL, 34.05 mmol) in acetic acid (40 mL) was added over 25 minutes to a stirred solution of N-[(2,6-dimethoxy-1-naphthalenyl)-carbonyl]-N-methylglycine methyl ester (10.70 g, 33.72 mmol, described in Example 2) in acetic acid (120 mL). After an additional 10 minutes the reaction was diluted with water (900 mL) and $NaHSO_3$ (2.0 g) was added. The resulting precipitate was collected by filtration, washed with water and dried to give 8.93 g (67% yield) of the title compound, m.p. 142°–144° C.

NMR (400 MHz, $CDCl_3$) Z-Rotamer: δ2.83 (s, 3H), 3.83 (d, 1H, J=17.3 Hz), 3.84 (s, 3H), 3.95 (s, 3H), 3.99 (s, 3H), 5.04 (d, 1H, J=17.3 Hz), 7.34 (d, 1H, J=9.3 Hz), 7.35 (d, 1H, J=9.4 Hz), 7.96 (d, 1H, J=9.3 Hz), 8.27 (d, 1H, J=9.4 Hz);

E-Rotamer: δ3.30 (s, 3H), 3.55 (s, 3H), 3.80 (d, 1H), 3.91 (s, 3H), 3.96 (d, 1H), 3.98 (s, 3H), 7.26 (d, 2H), 7.32 (d, 2H), 7.71 (d, 1H), 8.26 (d, 1H);

Signals due to rotamers appear in a ratio of 5:1 for Z- and E-rotamers respectively;

IR (KBr): 2950, 1735, 1635 cm$^{-1}$;

Anal. Calcd.: C, 51.53; H, 4.58; N, 3.53%. Found: C, 51.41; H, 4.52; N, 3.91%.

EXAMPLE 4

Preparation of N-[[2,6-Dimethoxy-5-(trifluoromethyl)-1-naphthalenyl]carbonyl]-N-methylglycine Methyl Ester A mixture of N-[5-bromo-2,6-dimethoxy-1-naphthalenyl)carbonyl]-N-methylglycine methyl ester (6.24 g, 15.7 mmol, described in Example 3), copper (I) iodide (11.99 g, 62.9 mmol), 1-methyl-2-pyrrolidinone (300 mL), and sodium trifluoroacetate (17.08 g, 12.6 mmol) was heated at 180° C. for 2 hours under an argon atmosphere. Upon cooling the residue was suspended in water (1 L) and ethyl ether (2 L) and potassium cyanide (30 g) were added with stirring. The organic layer was separated and washed sequentially with saturated $NaHCO_3$, water (3X), saturated NaCl and then dried over $Na_2SO_4$. After concentration, silica gel chromatography using 10:1 $CH_2Cl_2$:ethyl acetate as eluent gave 4.32 g (71% yield) of the title compound as a pale brown oil.

NMR (200 MHz, CDCl$_3$): δ2.84, 3.29 (2s, 4:1 ratio, 3H), 3.5–4.0 (m, 10H), 5.05 (d, 1H, J=17 Hz), 7.25–7.45 (m, 2H), 7.85–8.3 (m, 2H);

IR (CHCl$_3$): 3020, 2960, 1750, 1640 cm$^{-1}$;

High resolution mass spectrometry: C$_{18}$H$_{18}$F$_3$NO$_5$ Requires: 385.1137 Found: 385.1133.

EXAMPLE 5

Preparation of 6-Methoxy-2-(phenylmethoxy)-1-naphthalenecarboxaldehyde

1-Propanethiol (12.8 mL, 0.141 mol) was added over a 20 minute period to a suspension of sodium hydride (2.92 g, 0.122 mol) in N,N-dimethylformamide at 0° C. under a nitrogen atmosphere. To the resulting solution was added a solution of 2,6-dimethoxy-1-naphthalenecarboxaldehyde [21.6 g, 0.100 mol, described by N. P. Buu-Hoï et al, J. Chem. Soc., 2776 (1955)] in 100 mL of N,N-dimethylformamide, and the mixture was heated at 50°–60° C. for 3 hours. Anhydrous K$_2$CO$_3$ (28 g, 0.20 mol) and benzyl bromide (28.6 mL, 0.24 mol) were added and heating was continued for 2 hours. The mixture was cooled to room temperature overnight, then concentrated under vacuum. The residue was dissolved in water (800 mL) and ethyl acetate (1 L). The organic phase was collected and washed successively with 1M KOH, (400 mL), water (200 mL), and saturated NaCl and then dried over Na$_2$SO$_4$. After filtration and evaporation of the solvent, the residue was recrystallized from absolute ethanol to give 19.6 g, of the title compound as a yellow solid, m.p. 115°–117° C.

NMR (200 MHz, CDCl$_3$): δ3.91 (s, 3H), 5.31 (s, 2H), 7.08 (d, 1H, J=2 Hz), 7.2–7.5 (m, 7H), 7.95 (d, 1H, J=7 Hz), 9.21 (d, 1H, J=8 Hz), 10.94 (s, 1H);

IR (KBr): 1650 cm$^{-1}$;

Anal. Calcd.: C, 78.06; H, 5.52%. Found: C, 77.79; H, 5.56%.

EXAMPLE 6

Preparation of 5-Bromo-6-methoxy-2-(phenylmethoxy)-1-naphthalenecarboxaldehyde Bromine (3.22 mL, 62.5 mmol) was dissolved in 60 mL of glacial acetic acid and added, over a 20 minute period, to a soluton of 6-methoxy-2-(phenylmethoxy)-1-naphthalenecarboxaldehyde (17.4 g, 59.5 mmol, described in Example 5) in 270 mL of glacial acetic acid at 45° C. The resulting suspension was allowed to cool for 1 hour, then the precipitate was collected by filtration and washed thoroughly with absolute ethanol. The solid was suspended in 170 mL of toluene and concentrated by distillation at ambient pressure until about 30 mL remained then allowed to stand at room temperature overnight. The precipitate which formed upon cooling was collected by filtration and washed with hexane to give 18.14 g of the title compound as a yellow powder, m.p. 214°–220° C.

NMR (200 MHz, DMSO-d$^6$): δ3.96 (s, 3H), 5.46 (s, 2H), 7.3–7.7 (m, 6H), 7.83 (d, 1H), 8.47 (d, 1H), 9.14 (d, 1H), 10.79 (s, 1H);

IR (KBr): 1660 cm$^{-1}$;

Anal. Calcd.: C, 61.47; H, 4.07%. Found: C, 61.79; H, 4.24%.

EXAMPLE 7

Preparation of 6-Methoxy-2-(phenylmethoxy)-5-(trifluoromethyl)-1-naphthalenecarboxaldehyde A suspension of copper (I) iodide (35.5 g, 0.186 mol), trifluoroacetic acid, sodium salt (50 g, 0.37 mol), and 5-bromo-6-methoxy-2-(phenylmethoxy)-1-naphthalenecarboxaldehyde (17.3 g, 0.047 mol, described in Example 6) in anhydrous 1-methyl-2-pyrrolidinone (150 mL) was stirred vigorously and heated at 180° C. under argon for 1.5 hours, then cooled. The mixture was then suspended in 1 L of water and 1 L of ether and filtered through Solka-Floc*. The filtrate was separated into two phases and the ether layer was washed with water (3X) and then washed with saturated NaCl and dried over Na$_2$SO$_4$. The Solka-Floc filter cake was then washed thoroughly with dichloromethane and the filtrate was washed with water (3X), and then with brine and dried over Na$_2$SO$_4$. After filtration and concentration, the residues from the ether and dichloromethane solutions were combined, dissolved in dichloromethane (250 mL) and filtered through silica gel with additional dichloromethane. The filtrate was concentrated and chromatographed on silica gel with 1:1 hexane:dichloromethane to give 9.8 g (58% yield) of the title compound of suitable purity for subsequent reaction, m.p. 143°–145° C. (from ethanol).

*Solka-Floc is a trademark for a powdered cellulose product derived by mechanical communition of purified wood pulp.

NMR (200 MHz, CDCl$_3$): δ3.99 (s, 3H), 5.34 (s, 2H), 7.3–7.5 (m, 7H), 8.42 (d, 1H), 9.52 (d, 1H), 10.96 (s, 1H);

IR (CHCl$_3$): 1670 cm$^{-1}$;

Anal. Calcd.: C, 66.67; H, 4.20%. Found: C, 66.61; H, 4.17%.

EXAMPLE 8

Preparation of 6-Methoxy-2-(phenylmethoxy)-5-(trifluoromethyl)-1-naphthalnecarboxylic Acid A homogeneous mixture of 6-methoxy-2-(phenylmethoxy)-5-(trifluoromethyl)-1-naphthalenecarboxaldehyde (7.98 g, 22.15 mmol, described in Example 7), p-dioxane (80 mL), tert-butanol (80 mL), acetic acid (8 drops), and resorcinol (3.41 g, 31 mmol) was stirred at about 80° C. while a solution of sodium chlorite (3.00 g, 80%, 27 mmol) in water (20 mL) was added. The reaction was allowed to stir and cool for 30 minutes, whereupon a precipitate formed. The suspension was then concentrated under vacuum and the residue was partitioned between ethyl acetate and 1M HCl. The organic extracts were washed sequentially with 1M HCl, water, saturated sodium chloride and dried over sodium sulfate. Concentration and recrystallization of the residue from ethanol/water and subsequent drying afforded the title compound (6.77 g, 81% yield), m.p. 171°–175° C.

NMR (200 MHz, CDCl$_3$): δ3.99 (s, 3H), 5.34 (s, 2H), 7.2–7.6 (m, 7H), 8.32 (d, 1H), 8.58 (d, 1H);

IR (KBr): 3250, 1710 cm$^{-1}$;

Anal. Calcd.: C, 63.83; H, 4.02%. Found: C, 63.84; H, 3.98%.

EXAMPLE 9

Preparation of N-[[6-Methoxy-2-(phenylmethoxy)-5-(trifluoromethyl)-1-naphthalenyl]carbonyl]-N-methylglycine Methyl Ester A solution of oxalyl chloride (0.51 mL, 5.8 mmol) in $CH_2Cl_2$ (6 mL) was added dropwise to a suspension of 6-methoxy-2-(phenylmethoxy)-5-(trifluoromethyl)-1-naphthalenecarboxylic acid (2.00 g, 5.3 mmol, described in Example 8) in 50 mL of $CH_2Cl_2$ under a nitrogen atmosphere. The suspension became homogeneous upon stirring for 1.5 hours. The mixture was then placed under mild vacuum for about 5 minutes to remove the dissolved gases and then was transfered via syringe to a flask containing a suspension of N-methylglycine methyl ester hydrochloride (1.11 g, 8.0 mmol) and triethylamine (3.7 mL, 27 mmol) in 50 mL of $CH_2Cl_2$. The suspension was stirred for 20 hours then was poured into additional $CH_2Cl_2$ and 1M $H_3PO_4$. The organic phase was separated and washed successively with 1M $H_3PO_4$, water, saturated NaCl and then dried over $Na_2SO_4$. After filtration, concentration and silica gel chromatography with 20:1 $CH_2Cl_2$:ethyl acetate as eluent, the residue was recrystallized from ethanol to give 1.51 g (62% yield) of the title compound as a white powder, m.p. 95°–98° C.

NMR (200 MHz, $CDCl_3$): δ2.84 (s, 3H), 3.80 (d, 1H, J=17 Hz), 3.84 (s, 3H), 3.96 (s, 3H), 5.04 (d, 1H, J=17 Hz), 5.26 (s, 2H), 7.2–7.5 (m, 7H), 8.1–8.3 (m, 2H);

IR (KBr): 1740, 1640 $cm^{-1}$;

Anal. Calcd.: C, 62.47; H, 4.80; N, 3.03%. Found: C, 62.17; H, 5.03; N, 2.93%.

I claim:

1. A process for producing compounds of formula (II)

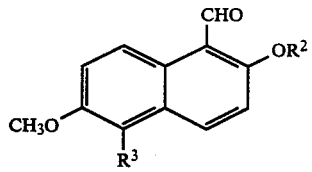

wherein $R^2$ is lower alkyl containing 2 to 6 carbon atoms or aryl(lower)alkyl wherein lower alkyl contains 1 to 6 carbon atoms and $R^3$ is hydrogen which comprises reacting an aldehyde of formula (II) wherein $R^2$ is methyl and $R^3$ is hydrogen with a nucleophilic sulfide demethylating agent and reacting the resulting phenolate salt with an alkylating agent of formula $R^2X$ wherein $R^2$ is the desired lower alkyl containing 2 to 6 carbon atoms or aryl(lower)alkyl wherein (lower)alkyl contains 1 to 6 carbon atoms and X is bromine, iodine, $OSO_3R^2$, or a sulfonate to produce the desired compound of formula (II).

2. A process according to claim 1 for producing the compound of formula (II) wherein $R^2$ is phenylmethyl and $R^3$ is hydrogen.

* * * * *